US011786580B2

(12) United States Patent
Waller et al.

(10) Patent No.: US 11,786,580 B2
(45) Date of Patent: Oct. 17, 2023

(54) VIP AND VIP AGONISTS, NANOPARTICLES, AND USES IN INFLAMMATORY T-CELL MEDIATED DISEASE

(71) Applicant: Emory University, Atlanta, GA (US)

(72) Inventors: Giacomo Waller, Atlanta, GA (US); Yiwen Li, Atlanta, GA (US); Edmund Waller, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/050,348

(22) PCT Filed: Apr. 23, 2019

(86) PCT No.: PCT/US2019/028820
§ 371 (c)(1),
(2) Date: Oct. 23, 2020

(87) PCT Pub. No.: WO2019/240881
PCT Pub. Date: Dec. 19, 2019

(65) Prior Publication Data
US 2021/0187076 A1 Jun. 24, 2021

Related U.S. Application Data

(60) Provisional application No. 62/661,214, filed on Apr. 23, 2018.

(51) Int. Cl.
*A61K 38/26* (2006.01)
*A61K 9/00* (2006.01)
*A61K 9/12* (2006.01)
*A61K 47/24* (2006.01)
*A61K 38/22* (2006.01)
*C07K 14/575* (2006.01)
*A61K 47/69* (2017.01)

(52) U.S. Cl.
CPC ............ *A61K 38/26* (2013.01); *A61K 9/0075* (2013.01); *A61K 9/124* (2013.01); *A61K 47/24* (2013.01); *A61K 47/6935* (2017.08)

(58) Field of Classification Search
CPC .. A61K 38/26; A61K 9/0075; A61K 47/6935; A61K 38/2278; A61K 47/26; C07K 14/57563
See application file for complete search history.

(56) References Cited

U.S. PATENT DOCUMENTS

| 7,901,666 | B1* | 3/2011 | Sung ................... A61K 9/5146 424/1.73 |
| 9,458,217 | B2 | 10/2016 | Waller et al. |
| 9,669,092 | B2 | 6/2017 | Waller et al. |
| 2002/0117170 | A1 | 8/2002 | Platz et al. |
| 2005/0279349 | A1 | 12/2005 | Patton et al. |
| 2013/0302351 | A1* | 11/2013 | Waller ................... A61P 31/12 424/229.1 |
| 2016/0045572 | A1 | 2/2016 | Shandler et al. |
| 2016/0187323 | A1 | 6/2016 | Farokhzad et al. |
| 2016/0220642 | A1* | 8/2016 | Sadeghi ................. A61P 43/00 |

FOREIGN PATENT DOCUMENTS

WO     2013051900     4/2013

OTHER PUBLICATIONS

International Search Report and Written Opinion issued for Application No. PCT/US2019/028820, dated Jan. 17, 2020.
Delgado et al.: "Vasoactive intestinal peptide prevents experimental arthritis by downregulating both autoimmune and inflammatory components of the disease", Nat Med., vol. 7, No. 5, 2001, pp. 563-568, XP002423625, DOI: 10.1038/87887.
Hoekman, John et al.: "Aerosol Stable Peptide-Coated Liposome Nanoparticles: A Proof-of-Concept Study with Opioid Fentanyl in Enhancing Analgesic Effects and Reducing Plasma Drug Exposure", J Pharm Sci., vol. 103, No. 8, 2014, pp. 2231-2239, XP055707646, DOI: 10.1002/jps.24022.
Prasse et al.: "Inhaled Vasoactive Intestinal Peptide Exerts Immunoregulatory Effects in Sarcoidosis", Am J Respir Crit Care Med., vol. 182, No. 4, 2010, pp. 540-548, XP008127269, DOI: 10.1164/rccm.200909-1451OC.
Petkov, Ventzislav et al.: "Vasoactive intestinal peptide as a new drug for treatment of primary pulmonary hypertension", J Clin Invest., vol. 111, No. 9, 2003, pp. 1339-1346, XP055707647, DOI: 10.1172/JCI200317500.
Tan, Xiaogang, et al. "A 5-microRNA signature for lung squamous cell carcinoma diagnosis and hsa-miR-31 for prognosis." Clinical cancer research 17.21 (2011): 6802-6811.
Li, Jian-Ming, et al. "VIPhyb, an antagonist of vasoactive intestinal peptide receptor, enhances cellular antiviral immunity in murine cytomegalovirus infected mice." PloS one 8.5 (2013): e63381.
Li, Jian-Ming, et al. "Pharmacological inhibition of VIP signaling enhances antiviral immunity and improves survival in murine cytomegalovirus-infected allogeneic bone marrow transplant recipients." Blood, The Journal of the American Society of Hematology 121.12 (2013): 2347-2351.
Li, Jian-Ming, et al. "Absence of vasoactive intestinal peptide expression in hematopoietic cells enhances Th1 polarization and antiviral immunity in mice." The Journal of Immunology 187.2 (2011): 1057-1065.

(Continued)

*Primary Examiner* — Mina Haghighatian
(74) *Attorney, Agent, or Firm* — Meunier Carlin & Curfman LLC

(57) ABSTRACT

In certain embodiments, this disclosure relates to VIP and VIP agonists, optionally conjugated to nanoparticles, for use in methods of treating inflammatory T cell-mediated diseases or conditions, e.g., treating or preventing GvHD. In certain embodiments, this disclosure relates to methods of pulmonary administration of VIP and VIP agonists, optionally conjugated to nanoparticles. In certain embodiments, this disclosure contemplates nanoparticles disclosed herein.

3 Claims, 3 Drawing Sheets
Specification includes a Sequence Listing.

(56) References Cited

OTHER PUBLICATIONS

Petersen, Christopher T., Jian-Ming Li, and Edmund K. Waller. "Administration of a vasoactive intestinal peptide antagonist enhances the autologous anti-leukemia T cell response in murine models of acute leukemia." OncoImmunology 6.5 (2017): e1304336.

Wang, Xiaojian, et al. "Mechanisms of antigen presentation to T cells in murine graft-versus-host disease: cross-presentation and the appearance of crosspresentation." Blood, The Journal of the American Society of Hematology 118.24 (2011): 6426-6437.

Schudel, Alex, et al. "S-Nitrosated Polypropylene Sulfide Nanoparticles for Thiol-Dependent Transnitrosation and Toxicity Against Adult Female Filarial Worms." Advanced healthcare materials 4.10 (2015): 1484-1490.

* cited by examiner

VIP AND VIP AGONISTS, NANOPARTICLES, AND USES IN INFLAMMATORY T-CELL MEDIATED DISEASE

CROSS-REFERENCE TO RELATED APPLICATIONS

This is the National Stage of International Application No. PCT/US2019/028820 filed Apr. 23, 2019, which claims the benefit of U.S. Provisional Application No. 62/661,214 filed Apr. 23, 2018. The entirety of each of these applications is hereby incorporated by reference for all purposes.

STATEMENT REGARDING FEDERALLY SPONSORED RESEARCH OR DEVELOPMENT

This invention was made with government support under CA188523 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18101PCT_ST25.txt. The text file is 2 KB, was created on Apr. 23, 2019, and is being submitted electronically via EFS-Web.

BACKGROUND

Allogeneic hematopoietic stem cell transplantation (Allo-HSCT) can treat hematological malignancies through the graft versus host effect mediated by donor cells. When multipotent hematopoietic stem cells and other immune cells of the bone marrow are introduced to a recipient transplanted naïve and donor T cells expand in the recipient, recognize, and eliminate residual malignant cells via adaptive immune pathways. The major clinical challenge in the more widespread clinical use of allo-HSCT is graft-versus-host-disease (GvHD). Recipient alloantigen is presented to donor T cells that attack non-malignant epithelial tissues and organs. Thus, there is a need to identify improved methods for treating hematological malignancies using stem cell transplantation.

Li et al report modulation of graft-versus-leukemia in allogeneic transplants by antagonizing vasoactive intestinal peptide signalling. Cancer Res, 2016, 76(23):6802-681. See also Li et al. PLoS One. 2013, 8(5):e63381; Li et al., Blood. 2013, 121(12):2347-51, Li et al., J Immunol. 2011, 187(2): 1057-65; U.S. Pat. Nos. 9,458,217 and 9,669,092; and U.S. Published Application number 2013/0302351. Petersen et al report administration of a vasoactive intestinal peptide antagonist enhances the autologous anti-leukemia T cell response in murine models of acute leukemia. Oncoimmunology. 2017, 6(5):e1304336.

References cited herein are not an admission of prior art.

SUMMARY

In certain embodiments, this disclosure relates to VIP and VIP agonists, optionally conjugated to nanoparticles, for use in methods of treating inflammatory T cell-mediated diseases or conditions. In certain embodiments, this disclosure relates to methods of treating graft verse host disease (GvHD) or an inflammatory autoimmune disease comprising administration an effective amount of vasoactive intestinal polypeptide or vasoactive intestinal polypeptide agonist to a subject in need thereof. In certain embodiments, the VIP or VIP agonist, optionally conjugated to nanoparticle, is administered in an aerosolized form. In certain embodiments, this disclosure relates to methods of pulmonary administration for any of the methods reported herein.

In certain embodiments, this disclosure relates to methods of treating or preventing inflammatory diseases mediated by T cell such as autoimmune diabetes, scleroderma, MS, and graft versus host disease. In certain embodiments, this disclosure relates to methods of using local administration of vasoactive intestinal polypeptide to modulate the systemic immune responses throughout the body.

In certain embodiments, the VIP or VIP agonist is given by sub-cutaneous injection. In certain embodiments, the VIP or VIP agonist is given by inhalation to deliver drug to the pulmonary alveoli. In certain embodiments, the VIP or VIP agonist is administered by a hand-held delivery device driven by compressed gas. In certain embodiments, the VIP or VIP agonist is dissolved in a solution of sterile saline and administered as an aerosol. In certain embodiments, the VIP or VIP agonist is coupled to a nanoparticle thereby improving the half-life of the vasoactive intestinal polypeptide in the alveolar space.

In certain embodiments, the nanoparticle is 20 to 40 nanometers in diameter. In certain embodiments, the nanoparticle is composed of biodegradable and biocompatible polyethylene glycol. In certain embodiments, the VIP or VIP agonist is dissolved in a solution of sterile saline and administered as an aerosol.

In certain embodiments, this disclosure relates to methods of treating inflammatory autoimmune disease by administration of an aerosolized form of vasoactive intestinal polypeptide. In certain embodiments, the vasoactive intestinal polypeptide is prepared as a dry powder with an inert carrier which is administered by a hand-held delivery device driven by compressed gas. In certain embodiments, the vasoactive intestinal polypeptide is dissolved in a solution of sterile saline and administered as an aerosol. In certain embodiments, the vasoactive intestinal polypeptide is coupled to a nanoparticle thereby improving the half-life of the vasoactive intestinal polypeptide in the alveolar space.

In certain embodiments, the nanoparticle is 20 to 40 nanometers in diameter. In certain embodiments, the nanoparticle is composed of biodegradable and biocompatible polyethylene glycol. In certain embodiments, the VIP or VIP agonist is composed of the sequence HSDAVFTDNYTRLRKQMAVKKYLNSILN (SEQ ID NO: 1). In certain embodiments, sequence of vasoactive intestinal polypeptide is modified to include a C-terminal link to or composed of polyglycine, four glycines, a serine, and a terminal cysteine in order to facilitate coupling to the nanoparticle: HSDAVFTDNYTRLRKQMAVKKYLN-SILNGGGGSC (SEQ ID NO: 2).

DETAILED DESCRIPTION

Figure 1A:
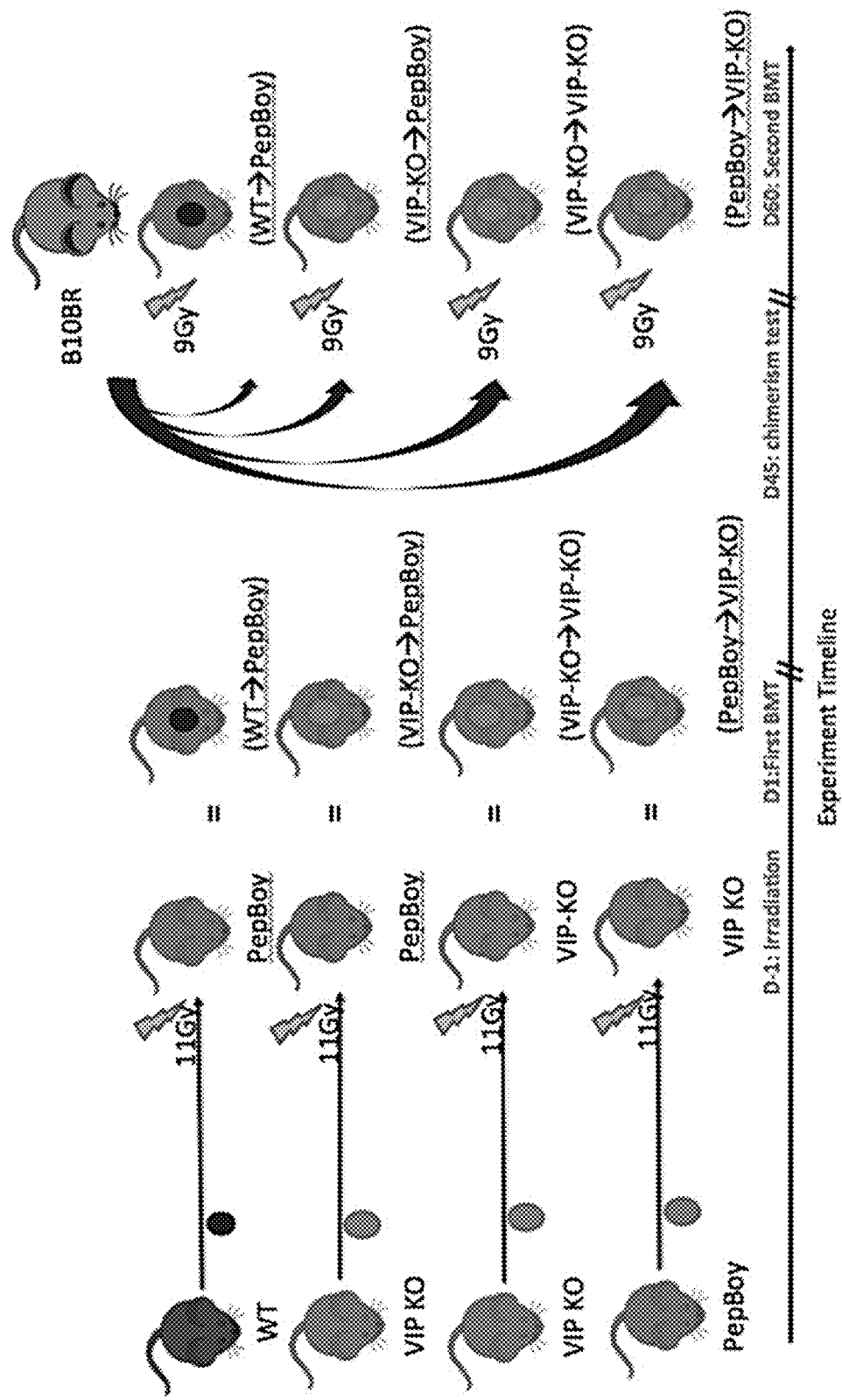
FIG. 1A illustrates tests of the timeline of experiment design that were performed resulting in data indicating VIP expression on on-hematopoietic tissues in radiation chimeric recipients was sufficient to prevent GvHD lethality after second allogeneic BMT. Lethally irradiated (11Gy in 2 equal splits 3-4 hours apart on D-1) C57/BL6 WT, VIP-KO or PepBoy mice were infused with 5M TCD corresponding BM for syngeneic transplant to create control mice with VIP production in both hematopoietic or non-hematopoietic cells or lacked VIP production in both hematopoietic or non-hematopoietic cells and to create radiation chimeras either lacked VIP production in hematopoietic or non-hematopoietic compartments. On D45 post syngeneic transplant, submandibular bleeding approach was used to collect blood testing for donor chimerism for WT to PepBpy (CD45.2 to CD45.1), VIP-KO to PepBoy (CD45.2 to CD45.1) and PepBoy to VIP-KO (CD45.1 to CD45.2). On D59 post syngeneic transplant, control and radiation chimera recipients were lethally irradiated (9Gy equally split in 2 dosage) and were infused with 5M TCD BM plus 1 or $3 \times 10^6$ splenocytes from B10. BR mice. Survival rate was recorded daily.
Figure 1B:
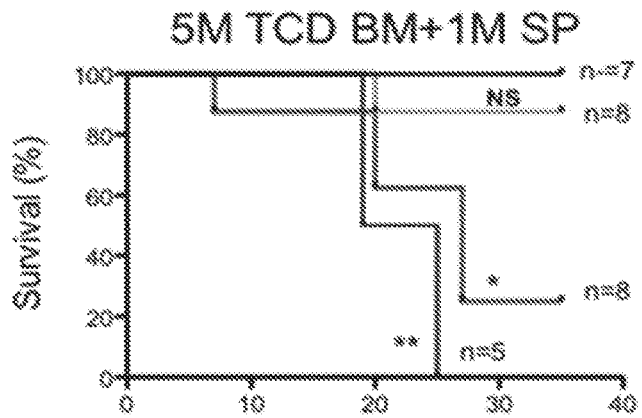
FIG. 1B shows a Kaplan-Meier survival plot of radiation chimera infused with 5M TCD BM plus $1 \times 10^6$ B10.BR splenocytes.
Figure 1C:
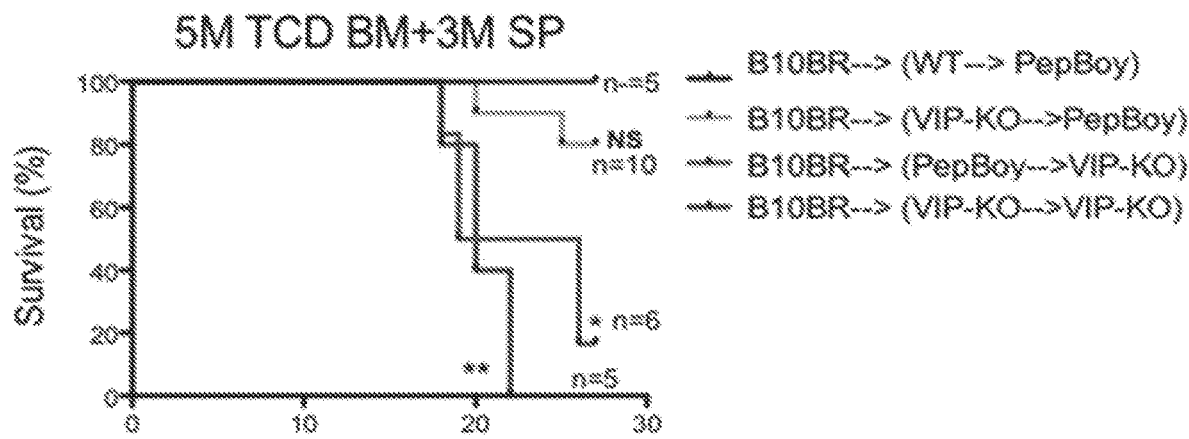
FIG. 1C shows a Kaplan-Meier survival plot of radiation chimera infused with 5M TCD BM plus $3 \times 10^6$ B10.BR splenocytes.
Figure 1D:
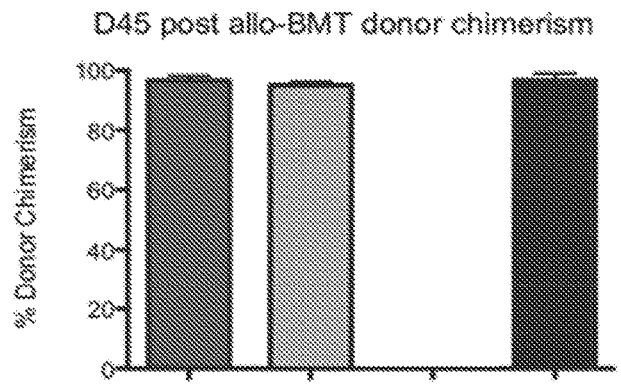
FIG. 1D shows donor chimerism on D45 post the 1st syngeneic transplant in four radiation chimeras.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

The terms "vasoactive intestinal peptide" and "VIP" refer to (SEQ ID NO: 1) HSDAVFTDNYTRLRKQMAVK-KYLNSILN unless the context suggests otherwise. VIP is a multifunctional endogenous polypeptide that modulates both innate and adaptive immunity at multiple levels of immune cell differentiation and activation. A "VIP agonist" refers to derivatives of VIP that bind receptors that bind vasoactive intestinal peptide receptors binds having the same or increased affinity as VIP. VIP binds to three G protein-coupled receptors, with high affinity binding to VPAC1, VPAC2 and lower affinity binding to PAC1.

VPAC1 is constitutively expressed on lymphocytes and dendritic cells while VPAC2 is expressed on immune cells upon stimulation. Contemplated "VIP agonists" include prodrugs of VIP, conjugates, or larger amino acid sequences that contain the amino acid sequence of VIP.

VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors-VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulphur atom or replacing an amino group with a hydroxyl group or vice versa. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A Method of Treating Inflammatory T Cell-Mediated Disease by Administration of Aerosolized Vasoactive Intestinal Polypeptide and Derivative Drugs Inflammatory diseases mediated by T cell are a major cause of morbidity and mortality and include autoimmune diabetes, scleroderma, MS, and graft versus host disease. Reactive T cells circulated in the blood and home to and damage target tissues that express cognate ligands for chemokine receptors present on T cells. All T cells circulate through the pulmonary vascular system and are exposed to the local cytokine milieu of and around the alveolar capillaries. The lung tissue is richly innervated by neurons that express vasoactive intestinal polypeptide leading to very high local concentrations of this immune-regulatory peptide in and around the pulmonary capillaries. Intra-tracheal administration of an aerosolized vasoactive intestinal polypeptide leads to high local concentrations in the pulmonary alveoli that diffused into interstitial space and the pulmonary capillaries. High concentrations of vasoactive intestinal polypeptide in the pulmonary capillaries attenuate the reactivity of T cells increasing frequencies of regulatory T cells and shifting T cell polarization from TH1 to TH2 immune responses thereby attenuating allo-reactive diseases caused by activated T cell subsets. The present disclosure describes an approach to treat inflammatory diseases mediated by T cell using local administration of vasoactive intestinal polypeptide modulate the systemic immune responses throughout the body.

In certain embodiments, this disclosure relates to methods of treating inflammatory autoimmune disease by administration of an aerosolized form of vasoactive intestinal polypeptide of VIP agonist. In certain embodiments, the vasoactive intestinal polypeptide is prepared as a dry powder with an inert carrier which is administered by a hand-held delivery device driven by compressed gas. In certain embodiments, the vasoactive intestinal polypeptide is dissolved in a solution of sterile saline and administered as an aerosol. In certain embodiments, the vasoactive intestinal polypeptide is coupled to a nanoparticle thereby improving the half-life of the vasoactive intestinal polypeptide in the alveolar space.

In certain embodiments, this disclosure relates to nanoparticles.

In certain embodiments, the nanoparticle is 20 to 40 nanometers in size. In certain embodiments, the nanoparticle is composed of biodegradable and biocompatible polyethylene glycol. In certain embodiments, the vasoactive intestinal polypeptide is composed of the sequence HSDAVFTDNYTRLRKQMAVKKYLNSILN (SEQ ID NO: 1). In certain embodiments, the sequence of vasoactive intestinal polypeptide is modified to include a C-terminal link or composed of four glycines, a serine, and a terminal cysteine in order to facilitate coupling to the nanoparticle:

(SEQ ID NO: 2)
HSDAVFTDNYTRLRKQMAVKKYLNSILNGGGGSC.

Methods of Preventing Graft-Versus-Host Disease (GvHD) by Pulmonary Administration Allogeneic hematopoietic stem cell transplantation (allo-HSCT) are used to treat relapsed hematological malignancies mediated by donor cells. When multipotent hematopoietic stem cells and other immune cells are introduced to the recipient conditioned and lympho-depleted by chemotherapy and/or radiotherapy, transplanted naïve and bone marrow-derived donor T cells expand in the recipient and recognize and eliminate residual leukemia and other malignant cells via adaptive immune pathways. The major clinical challenge in the more widespread clinical use of allo-HSCT is graft-versus-host-disease (GvHD), in which recipient alloantigen is presented to donor T cells that attack non-malignant epithelial tissues and organs leading to high morbidity and mortality. Thus, there is a need to identify methods that improve the beneficial effect from the deleterious GvHD.

The immune system has special mechanisms for dealing with pathogens that occupy intracellular space including cytotoxic T lymphocytes (CD8+ T cells) and helper T lymphocytes (CD4+ T cells). Major histocompatibility complexes (MHC) are molecules on the outside of cells that present pathogenic antigens for interaction with T cells receptors (TCRs) on CD8+ and CD4+ T cells.

Antigen expression cells (APCs), e.g., white blood cells (leukocytes) and dendritic cells, activate CD4+ T cells through interactions with Class II MHC molecules. Class I MHC molecules are on almost all cells of the body, including APCs, and activate CD8+ T cells. The structure of Class I and II MHC molecules differ from persons to person. However, the structure of Class I and II MHC molecules also have varying degrees amino acid sequence similarity (referred to as variant antigens) depending on the genetic profile of each individual.

Graft versus host disease (GvHD) is the deterioration of cells or tissues that are transplanted from a donor to a recipient due to the recognition by the immune system of the recipient that the cells or tissues are foreign. Thus, because Class I MHC are on more cells of the body, it is most desirable to transplant cells and tissues from people that have highest matching Class I MEW profiles followed by the highest matching Class II MEW profiles. Thus, in most transplant recipients, GvHD is due to activation of the immune system to mismatched Class II MEW molecules and other polymorphic proteins (minor histocompatibility antigens).

One option for treating cancers of the blood and bone marrow is to kill existing blood and marrow cells, e.g., through radiation or chemotherapy, and transplant similar cells from a healthy donor, referred to as an allogeneic hematopoietic stem cell transplant (allo-HSCT). Chemotherapy for bone marrow remission typically includes prednisone, vincristine, and an anthracycline drug; other drug plans may include L-asparaginase or cyclophosphamide. Another option is prednisone, L-asparaginase, and vincristine. Other options included methotrexate and 6-mercaptopurine (6-MP).

Hematopoietic cells can be obtained from suitably matched related or unrelated volunteer donors (allogeneic) or from the tissues of the subject (autologous). Sources of hematopoietic cells include the bone marrow, blood, or umbilical cord blood. One option is to obtain hematopoietic stem cells from a bone of a donor such as physically harvesting it from the pelvis. Hematopoietic stem cells (HSCs) may be obtained from peripheral blood by apheresis wherein blood is centrifuged and subsequently separated into plasma, leukocytes (white blood cells), and erythrocytes (red blood cells). The plasma typically contains HSCs and other cells such as, APCs and T-cells. Administering Granulocyte-colony stimulating factor to the donor prior to apheresis increases stem cell concentrations.

GvHD is believed to be due in part to stimulation of donor CD8+ T cells by APCs of the donor and recipient host through presentation of antigens in Class I MHC molecules. Exchange of membrane fragments and associated proteins between cells, termed trogocytosis, generates cross-dressed APCs. Wang et al. report that the transference of transmembrane proteins, such as MHC class I-peptide complexes, from irradiated hosts to donor dendritic cells (DCs), one from of APC cells, results in them having host antigens. See Blood. 2011, 118(24):6426-37. Cross-dressed donor DCs that acquire host MHC class I-peptide complexes are potent stimulators of T cells. CD11c is a type I transmembrane protein found at high levels on most human DCs. The presence of "cross-dressed" CD11c+ antigen presenting APCs cells expressing both donor and recipient type MHC-I molecules supports a "semi-direct" pathway of allo-activation. These APCs can efficiently present allo-antigens to both CD4+ and CD8+ T cells and activate immune responses that can lead to allograft rejection or GvHD.

The high frequencies of cross-dressed donor CD11c+ APCs following allo-HSCT indicates that semi-direct allo-antigen presentation can play an important role in the initiation of GvHD. Reducing the generation of cross-dressed APCs by pharmacological interruption of trogocytosis is an approach to reduce or prevent GvHD post allo-HSCT, targeting the semi-direct pathway of allo-antigen presentation.

The pleiotropic effects of VIP are mediated through its receptors widely distributed in the central nervous system and peripheral tissues (immune, pulmonary, GI and cardiovascular systems). VIP expression in immune cells represents a significant co-inhibitory pathway, as VIP signalling dampens systemic inflammatory responses and the in vivo immunomodulatory role of endogenous VIP produced by hematopoietic compartment has been confirmed by the higher frequencies of antiviral CD8 T cells detected in WT mice transplanted with bone marrow cells from VIP KO mice. The augmentation in antiviral response was attributed to the absence of hematopoietic VIP production as normal levels of neuronal VIP were produced in the bone marrow chimeric mice. In allo-BMT setting, GvHD is mediated by early activation of alloreactive donor T cells, which secondarily upregulate co-inhibitory pathway molecules, including VIP expression on T cells and dendritic cells. Whether absence in VIP expression by recipient cells would enhance donor T cell activation and increase GvHD in allo-BMT recipients was tested.

The longstanding challenges in clinical setting following allo-HSCT is the detrimental consequences of allo-reactive T cell induced GvHD, but yet T cell depletion of the graft exposes recipients to the high risk of poor engraftment and leukemia relapse. Consistent with these findings, both WT and VIP-KO recipients received allo-BMT with high dose of splenocytes ($3\times10^6$) had higher GvHD-induced mortality compared the corresponding WT and VIP-KO recipients received grafts with low-dose splenocytes ($1\times10^6$) or no splenocytes. Among the WT and VIP-KO recipients transplanted with same bone marrow plus splenocyte dosages (0, $1\times10^6$ or $3\times10^6$), VIP-KO recipients had reduced survival compared to WT recipients suggesting that the absence in endogenous VIP expression by recipient cells enhanced GvHD progression. Reduced survival in WT and VIP-KO group receiving BM only (73.3% vs 33.3% correspondingly) suggested higher levels of early graft rejection in VIP KO mice, possibly due to host versus graft effect of residual host T cells or NK cells in the absence of endogenous VIP. A potential caveat in interpreting the survival differences among WT and VIP-KO groups as a consequence of immune modulation is the possibility that the absence of endogenous VIP could result in enhanced sensitivity to irradiation. VIP-KO mice had comparable radiation sensitivity as WT mice by showing equivalent survival pattern among WT and VIP-KO groups received 11Gy irradiation split into two equal dosages in the absence of allo-BMT.

Cytokine storm is a signature step in GvHD pathogenesis. Th1, Th2 and Th17 cytokine production were measured in a time course among WT and KO recipients transplanted with 5M TCD BM plus $1\times10^6$ or $3\times10^6$ splenocytes. VIP signalling has been shown to inhibit pro-inflammatory Th1 polarization and favours anti-inflammatory Th2 differentiation in both in vivo and in vitro studies. Consistent with these reports, pro-inflammatory Th1 cytokines (IFN-γ and TNF-α) were consistently produced in significantly higher frequencies on CD4+ and CD8+ T cells in VIP-KO recipients received 5M TCD BM plus $1\times10^6$ or $3\times10^6$ splenocytes compared to WT recipients at the peak of post-transplant inflammation following allo-BMT. Significantly elevated CD4+ and CD8+ TNF-α Th1 cytokine production in VIP-KO recipients received $3\times10^6$ splenocytes are consistent with higher levels of inflammatory cytokines leading to increased death incidences in VIP-KO groups compared to the WT group. In addition, WT recipients transplanted with $3\times10^6$ splenocytes had significantly increased frequencies of CD8+IL4 and CD8+IL10 ($p<0.01$) compared to VIP-KO recipients on D19 and D5 correspondingly post allo-BMT, confirming greater anti-inflammatory Th2 polarization in the presence of endogenous VIP in transplant recipients.

T cells phenotypically characterized as Th17 cells plays a role in autoimmunity promoting inflammatory response in Crohn's disease. Previous studies have controversial conclusions on whether VIP signally negatively regulates Th17 differentiation and Th17 cytokine production. In experimental murine models of type I diabetes delayed disease onset and reduced level of IL17, RORγt and IL22 productions were observed after VIP administration, which indicates VIP exhibits inhibitory effect on Th17 polarization. However other the in vivo and in vitro experiments showed increased numbers of IL17+ T cells were correlated with increased exposure to TGFβ and VIP treatment for Langerhans cells, or for cultured human Th17 cells. In an allo-BMT experimental setting, it was found that significantly increased CD4+IL17 and CD8+IL17 correlated with significantly elevated RORγt level in VIP-KO recipients on D25 post allo-BMT compared to WT recipients received $3\times10^6$ splenocytes, which may contribute to the pro-inflammatory cytokine storm stage and GvHD maintenance.

Given the immunosuppressive nature of VIP and its production in immune cells, central and peripheral nervous system, it is important to be able to separate out which source of VIP production plays a more critical role in GvHD control. Thus, radiation chimeric mice were generated, in which either their hematopoietic or non-hematopoietic system lacked VIP production. The mice went through syngeneic transplant (VIP-KO to VIP-KO or WT B6 CD45.2 to PepBoy CD45.1) as controls to assess allo-BMT outcome. Analysis of the levels of donor chimerism after syngeneic transplant confirmed no significant differences among four chimeric mice groups. Following a second allogeneic transplant that included a donor T cells, significant differences in survival rates were seen across the radiation chimera groups demonstrating the contribution of VIP production in non-hematopoietic compartment in the transplant recipients in limiting GvHD, as well as a potential contribution by the host hematopoietic cells in the WT to VIP KO radiation chimeric mice.

To further characterize VIP production in the non-hematopoietic compartment of recipients post allo-BMT, a transgenic mouse was used in which the GFP was placed downstream of the VIP promoter. Non-transplanted VIP-GFP mice were used as controls to examine VIP production prior to allo-BMT. VIP-GFP+ cells were superimposable with MAP2+ staining in lung tissue, suggesting that the source of VIP production was from a neuronal origin. This finding is consistent with physiological phenomenon that the vagal nerve, as the tenth cranial nerve, is known for its extensive innervation of the neck, chest, and abdomen region. The efferent vagal nerve functions not only respiration modulation, but also has basic physiological functions of the cardiovascular, immune, and digestive systems. Eighty percent vagal neurons collect input from thoracic tissues, including lung and inputs from abdomen region and relay them back to the brain. A high percentage of VIP-GFP+ anuclear cell processes were also detected in host lungs on day 15 post-transplant, indicating that VIP production continues in host-type nerve cells after allogeneic transplantation. These data suggest the interesting hypothesis that VIP production by the extensive network of nerves cells in the lung may have an important role in regulating post-transplant immune responses. In addition, small portion of CD45+ VIP-GFP+ cells in host liver and spleen, but not in lung or intestines, were observed on day 15 post allo-BMT, suggesting that a minority of residual host leukocytes in immune and GvHD selected targeted organ continue to express VIP at this time-point. Overall, these data suggest that regulation of donor T-cell allo-reactivity and immune polarization by host neurons surrounding lung alveoli represents a promising avenue for pharmacological intervention of allo-reactive T cells and control of GVHD.

This disclosure relates to the use of VIP and VIP agonists to manage graft versus host disease (GVHD) in a subject after a hematopoietic stem cell transplant wherein pulmonary administration is contemplated. In certain embodiments, the subject has a blood or bone marrow cancer or condition.

In certain embodiments, the subject is immune compromised or the subject is an allogeneic bone marrow transplant donor or recipient. In typical embodiments, the subject is an organ transplant recipient, undergoing hemodialysis, diagnosed with cancer, receiving an immunosuppressive drug. In certain embodiments, the disclosure relates to methods of treating or preventing host verses graft disease in a subject comprising administering an effective amount of an VIP or VIP agonist to a subject that is to receive or received transplanted allogeneic tissue or cells. Typically, pulmonary administration is contemplated.

In certain embodiments, the subject received transplanted allogeneic hematopoietic stem cells. In certain embodiments, subject received transplanted allogeneic hematopoietic stem cells separated from peripheral blood. In certain embodiments, the subject received chemotherapy and/or radiation treatments prior to receiving transplanted allogeneic hematopoietic stem cells. In certain embodiments, the subject is a human.

In certain embodiments, the disclosure relates to methods of treating cancers or conditions of the blood and bone marrow comprising the steps of, exposing the subject to radiation and/or administering a chemotherapy agent to the subject; transplanting allogeneic hematopoietic stem cells into the subject; and administering vasoactive intestinal peptide of VIP agonist under conditions such that host verses graft disease is prevented or reduced. Typically, pulmonary administration is contemplated. In certain embodiments, the cancer or conditions are selected from leukemia, lymphoma, myeloma, and myelodysplasia. In certain embodiments, the cancers or conditions are selected from osteosarcoma, Ewing tumors, chordomas, chondrosarcomas, bone marrow failure, sickle cell disease, and thalassemia. In certain embodiments, pulmonary administration is contemplated.

In certain embodiments, subject is further administered one or more chemotherapy agents selected from imatinib, doxorubicin, cisplatin, carboplatin, etoposide, ifosfamide, cyclophosphamide, methotrexate, vincristine.

In certain embodiments, the subject is further administered a combination of cisplatin and doxorubicin.

In certain embodiments, the cancer or conditions are selected from leukemia, lymphoma, myeloma, and myelodysplasia.

In certain embodiments, the subject is further administered a chemotherapy agent, antibodies, directed at lymphoma cells.

In certain embodiments, the disclosure relates to the use of VIP or VIP agonists to prevent graft versus host disease (GVHD) in a subject after, before, or during a hematopoietic stem cell transplant.

In certain embodiments, the subject is administered a VIP or VIP agonist, after a hematopoietic stem cell transplant. In certain embodiments, the VIP or VIP agonist is administered for more than one month, two months, three months, four months, five months, six months, one year, one and one half years, or two years on a daily, bi-daily, or weekly basis after a hematopoietic stem cell transplant.

In certain embodiments, the subject is administered a VIP or VIP agonist, before a hematopoietic stem cell transplant. In certain embodiments, the VIP agonist is administered more than 3, hours, 5 hours, 10 hours, 24 hours, 2 days, 3 days, or 7 days, on a daily, bi-daily, or weekly basis.

Pharmaceutical Compositions

In certain embodiments, the disclosure contemplates pharmaceutical composition comprising VIP or VIP agonist, or nanoparticle thereof, or optionally other pharmaceutical agent, or pharmaceutically acceptable salts thereof, and a pharmaceutically acceptable excipient. In certain embodiments, the pharmaceutical composition is in the form of a sterilized pH buffered aqueous salt solution. In certain embodiments, the pharmaceutically acceptable excipient is aerosolizing agent or phospholipids. In certain embodiments, the aerosolizing agent is a hydrofluoroalkane, 1,1,1, 2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the phospholipid is dipalmitoylphosphatidylcholine, palmitoyl-oleoyl phosphatidylglycerol, phosphatidylglycerol, or combinations thereof.

In certain embodiments, the pharmaceutical compositions may be stored in a nebulizer, inhaler, or other container optionally sealed or under a pressure for propelling the pharmaceutical agent(s). The container may contain a spraying apparatus that is manually-actuated or pressurized. Metered dose inhalers (MDIs) typically have a handheld aerosol canister that, upon being pushed, releases an amount of medicine to inhale. Dry powder inhalers (DPIs) do not use a propellant to release the medicine. Instead, a dry powder form of the VIP agonist or nanoparticle thereof or agent is drawn into your lungs after a breath. In certain configurations, a container comprising the VIP or VIP agonist or nanoparticle thereof or agent is inserted a device. Pressing a button or section on the device pierces the container. One can breathe in the powder contained in the container through a mouthpiece on the device.

In certain embodiments, the pharmaceutical compositions may contain naturally or non-naturally occurring pulmonary surfactant compositions. Contemplated natural pulmonary surfactant compositions typically comprise 70-90% phospholipids (PC) such as dipalmitoylphosphatidylcholine (DPPC), phosphatidylcholine, and phosphatidylglycerol (PG); and 1-10% surfactant-associated proteins, apolipoproteins SP-A (SFTPA1), B (SFTPB), C (SFTPC) and D (SFTPD) (SP standing for "surfactant-associated protein"); and 1-10% Cholesterol (neutral lipids). Artificial pulmonary surfactants include colfosceril palmitate (Exosurf), a mixture of DPPC with hexadecanol and tyloxapol added as spreading agents; pumactant (Artificial Lung Expanding Compound or ALEC), a mixture of DPPC and PG; KL-4, composed of DPPC, palmitoyl-oleoyl phosphatidylglycerol, and palmitic acid, combined with a 21 amino acid synthetic peptide that mimics the structural characteristics of SP-B; and Venticute™, composed of DPPC, PG, palmitic acid and recombinant SP-C shares a nearly identical sequence with human SP-C except that the palmitoylated cysteines are absent and have been replaced with phenylalanines to eliminate protein oligomerization. Contemplated animal derived surfactants include beractant (Alveofact™), extracted from cow lung lavage fluid and (Survanta™), extracted from minced cow lung with additional DPPC, palmitic acid and tripalmitin; calfactant (Infasurf™), extracted from calf lung lavage fluid; and poractant alfa (Curosurf™)—extracted from material derived from minced pig lung.

In certain embodiments, the pharmaceutical compositions disclosed herein further comprise a respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate; a p38 antagonist such as losmapimod; a phosphodiesterase (PDE) inhibitor such as a methylxanthine, theophylline, and aminophylline; a selective PDE isoenzyme inhibitor, a PDE4 inhibitor and the isoform PDE4D, such as tetomilast, roflumilast, oglemilast, ibudilast, ronomilast; a modulator of chemokine receptor function such as vicriviroc, maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as setileuton, licofelone, quiflapon, zileuton, zafirlukast, or montelukast; and a myeloperoxidase antagonist such as resveratrol and piceatannol.

Effective doses may be extrapolated from dose-response curves derived from in vitro or animal model test systems. For VIP or VIP agonist, or nanoparticle thereof, or other agents, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of VIP agonist or nanoparticle thereof or agent may be reduced by enhancing uptake and tissue penetration by modifications such as, for example, lipidation and the inclusion of natural or artificial pulmonary surfactants.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, the pharmaceutical compositions is in solid form surrounded by an enteric coating, i.e., a polymer barrier applied on oral medication that prevents its dissolution or disintegration in the gastric environment. Compounds typically found in enteric coatings include methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, and combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be both natural and artificial pulmonary surfactants, sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with VIP or VIP agonist or nanoparticle thereof or agents disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising VIP or VIP agonist, or nanoparticle thereof, and agents disclosed herein and pharmaceutically acceptable excipient. In certain embodiments, this disclosure contemplates the production of a medicament comprising VIP or VIP agonist, or nanoparticle thereof, or agents disclosed herein and uses for methods disclosed herein.

In certain embodiments, the disclosure relates to pharmaceutical compositions comprising VIP or VIP agonist, or nanoparticle thereof, and agents disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and Viscoleo™), preparations incorporated into pulmonary surfactants (both natural and artificial), and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminium monostearate and gelatin.

Solid dosage forms for oral administration include capsules, tablets, pills, powders and granules. In such solid dosage forms, the VIP or VIP agonist, or nanoparticle thereof, or agents may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the VIP or VIP agonist, or nanoparticle thereof, and agents, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, VIP or VIP agonist, or nanoparticle thereof, and agents disclosed herein and a pharmaceutical carrier, are provided already in a combined dry form ready to be reconstituted together. In other embodiments, it is contemplated that VIP or VIP agonist or nanoparticle thereof and agents disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated VIP or VIP agonist, or nanoparticle thereof, or agents can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as inhalers, syringes, vials, tubes, etc. The pharmaceutical composition may then be applied via actuation or specific needles of the syringe or via suitable catheters. A typical diluent comprises water for injection, and NaCl (preferably 50 to 150 mM, especially 110 mM), $CaCl_2$) (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, this disclosure contemplates a kit comprising a pharmaceutical composition disclosed herein such as a VIP or VIP agonist, or nanoparticle thereof, or agent and a container optionally with a suitable diluent. Further components of the kit may be instructions for use, administration means, such as inhalers, syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

EXAMPLES

Nanoparticles

One can conjugate VIP-with a C-terminal amino acid sequence-GGGGSC (SEQ ID NO: 3) providing, HSDAVFTDNYTRLRKQMAVKKYLNSILNGGGGSC (SEQ ID NO: 2) to an average 30 nm Pluronic-stabilized polypropylene sulfide nanoparticles as described in Schudel et al S-nitrosated polypropylene sulfide nanoparticles, Adv. Healthcare Mater. 2015, 4, 1484-1490.

VIP Production in Non-Hematopoietic Compartment Post Allo-BMT Limits GvHD

Figure 2:
FIG. 2 illustrates tests performed indicating VIP-GFP+ producing host leukocytes can be detected at least for 15 days post allo-BMT. Lethally irradiated VIP-GFP B6 recipients were infused with 5M TCD BM plus $3 \times 10^6$ B10.BR splenocytes (n=5) and were sacrificed on D15 post allo-BMT. Intestine, lung, liver, thymus and spleen specimens were collected in OCT embedded cryomolds and frozen sections of the collected tissues were processed and sectioned.
Figure 3:
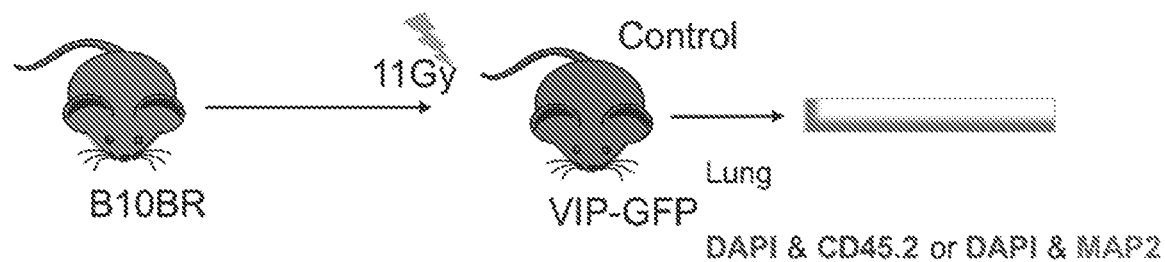
FIG. 3 illustrates tests performed indicating VIP-GFP+ producing neural cells can be detected at least for 15 days post allo-BMT. Control VIP-GFP B6 recipients (n=3) and were sacrificed. Lung specimens were collected in OCT embedded cryomolds and frozen sections of the collected tissues were processed and sectioned.
Figure 4:
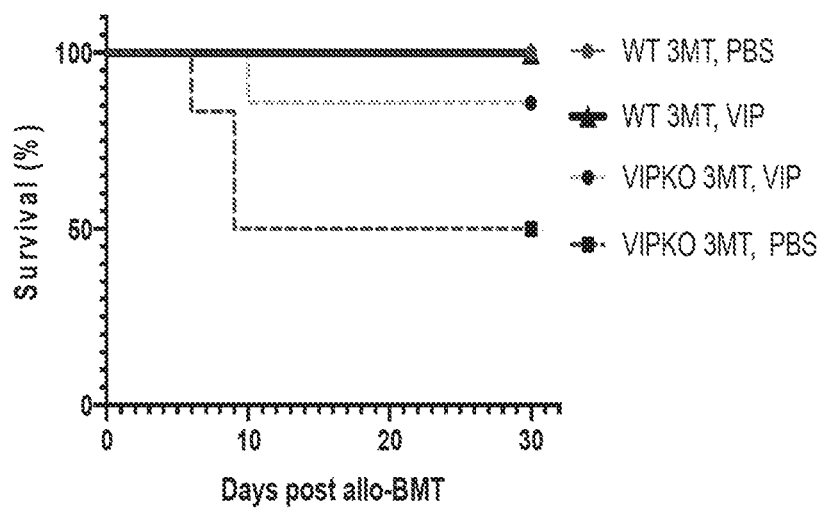
FIG. 4 shows data indicating short-term administration of VIP rescued VIP-KO recipients from GvHD induced lethality. Lethally irradiated WT and VIP-KO B6 recipients were infused with 5M TCD BM plus $3 \times 10^6$ B10.BR T cells. Administration of VIP (10 μgram/day) vs PBS from day 0 to day 10 rescued VIP-KO recipients from acute GvHD mortality after allo-BMT.

As VIP production is not restricted to the immune system, the role of VIP signalling exclusively mediated by recipient non-hematopoietic compartment (i.e., peripheral neurons) was investigated. Radiation chimeras were made via syngeneic transplants, where either the hematopoietic or non-hematopoietic compartment of recipients lacked VIP expression. Chimerism studies on day 45 post-BMT showed equivalent levels of donor chimerism within each group that received the same dose of donor bone marrow and splenocytes (FIG. 2D). B10BR mice were used as donors to perform a second allogeneic transplant on the radiation chimeras. Consistent survival differences were observed in chimeric recipients received 5M TCD BM plus 1×10⁶ or 3×10⁶ SP. Recipients that lacked VIP expression in both hematopoietic or non-hematopoietic compartments (VIP KO to VIP KO) had 0% survival at D25 post allo-BMT, whereas chimeric recipients that lacked VIP expression in hematopoietic compartment (VIP-KO to PepBoy) had significantly better survival than chimeric recipients lacked VIP expression in non-hematopoietic compartment (PepBoy to VIP-KO) (p<0.05). Notably, 100% survival was observed in recipients that did not lack VIP production in neither hematopoietic nor non-hematopoietic compartments (WT C57 Bl/6 to PepBoy).

plus 3×10⁶ splenocytes from WT B10.BR donors, and visualized VIP gene promoter activity as GFP expression in cells in recipient lymphoid tissues and GvHD target organs co-stained with DAPI and anti-CD45. Additional lung, liver and intestine were co-stained with DAPI and MAP2 for detection of neurons. Small number of CD45+ VIP-GFP+ cells were detected from in host spleen but not in liver, lung or intestines on day 15 post-transplant, suggesting that a small number of residual host leukocytes, particularly dendritic cells, continued to express VIP for at least 15 days post-transplant (FIG. 2). Additionally, a high frequency of VIP-GFP+ anuclear cell processes were seen in host lungs, indicating that relatively high level of VIP production continues in host-type nerve cells after allogeneic transplantation (FIG. 3).

---

SEQUENCE LISTING

<160> NUMBER OF SEQ ID NOS: 2

<210> SEQ ID NO 1
<211> LENGTH: 28
<212> TYPE: PRT
<213> ORGANISM: Artificial
<220> FEATURE:
<223> OTHER INFORMATION: Synthetic construct

<400> SEQUENCE: 1

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```

<210> SEQ ID NO 2
<211> LENGTH: 34
<212> TYPE: PRT
<213> ORGANISM: Artificial
<220> FEATURE:
<223> OTHER INFORMATION: Synthetic construct

<400> SEQUENCE: 2

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Gly Gly Gly Gly
            20                  25                  30

Ser Cys
```

---

Detection of VIP Production in Hematopoietic and Non-Hematopoietic Cells Up to D15 Post Allo-BMT To characterize the source of VIP produced by cells in transplant recipients, we used a transgenic mouse in which the GFP was placed down-stream of the VIP promoter. The original strain of VIP-GFP mice on a FVB/N background was back-crossed to C57BL/6 mice for more than 10 generations, using a PCR assay for GFP to track the presence of the transgene. We found the presence of the VIP-GFP transgene with VIP and GFP primers. Among non-transplanted VIP-GFP mice, VIP-GFP+ cells were super-imposable with MAP2+ in lung tissue, indicating neuronal origin of VIP in the lung.

Whether VIP production in host tissues persists after allogeneic transplantation was tested. C57/BL6 recipients expressing a GFP transgene under the control of the VIP promoter (n=10) were transplanted with 5×10⁶ TCD BM

The invention claimed is:

1. A method of treating autoimmune diabetes, scleroderma multiple sclerosis, (MS), or graft versus host disease comprising administering an effective amount of an aerosolized form of a vasoactive intestinal polypeptide (VIP) agonist to a subject in need thereof, wherein the VIP agonist comprises an amino acid sequence (SEQ ID NO: 2),
HSDAVFTDNYTRLRKQMAVKKYLNSILNGGGGSC
and wherein the VIP agonist is coupled to a nanoparticle.

2. The method of claim 1 in which the nanoparticle is 20 to 40 nanometers in diameter.

3. The method of claim 1 in which the nanoparticle is composed of biodegradable and biocompatible polyethylene glycol.

* * * * *